US009168030B2

(12) United States Patent
Dracker

(10) Patent No.: US 9,168,030 B2
(45) Date of Patent: Oct. 27, 2015

(54) ENVELOPE AND PROCUREMENT STAND FOR PLACENTAL TRANSPORT AND STEM CELL COLLECTION

(76) Inventor: Robert A. Dracker, Liverpool, NY (US)

( * ) Notice: Subject to any disclaimer, the term of this patent is extended or adjusted under 35 U.S.C. 154(b) by 450 days.

(21) Appl. No.: 13/584,100

(22) Filed: Aug. 13, 2012

(65) Prior Publication Data
US 2013/0040382 A1 Feb. 14, 2013

Related U.S. Application Data

(60) Provisional application No. 61/522,275, filed on Aug. 11, 2011, provisional application No. 61/522,280, filed on Aug. 11, 2011.

(51) Int. Cl.
C12M 1/00 (2006.01)
A61B 10/02 (2006.01)
A61B 17/34 (2006.01)
G01N 33/48 (2006.01)
G01N 1/28 (2006.01)
C12M 1/26 (2006.01)
C12M 3/00 (2006.01)

(52) U.S. Cl.
CPC ............ *A61B 10/02* (2013.01); *A61B 17/3403* (2013.01); *G01N 1/28* (2013.01); *G01N 33/48* (2013.01)

(58) Field of Classification Search
None
See application file for complete search history.

(56) References Cited

U.S. PATENT DOCUMENTS

| 4,437,586 A * | 3/1984 | Columbus ................. 222/181.2 |
| 2002/0002355 A1 | 1/2002 | Kuypers et al. |
| 2004/0034276 A1 | 2/2004 | Voellmicke et al. |
| 2005/0019908 A1 | 1/2005 | Hariri |
| 2008/0208158 A1 | 8/2008 | Goodman et al. |

OTHER PUBLICATIONS

International Search Report Form PCT/ISA/220, International Application No. PCT/US2012/050578, pp. 1-10, Dated Feb. 19, 2013.

* cited by examiner

Primary Examiner — Neil N Turk
(74) Attorney, Agent, or Firm — Blaine T. Bettinger; George R. McGuire; Bond Schoeneck & King

(57) ABSTRACT

A device for the transport of a placenta and a stand for the collection of stem cells from the placenta. The placental transport device comprising a cylindrical top portion and a cylindrical bottom portion together defining a placental storage region, with a hinge coupling the portions such that the placenta is enclosed inside the placental storage region when the cylindrical top and bottom portions are in a closed configuration. The stand comprising a base with a recess adapted to hold a placenta during stem cell collection solution loading, an upright back support, and an upper platform with a recess adapted to hold the placenta during collection of stem cells.

4 Claims, 6 Drawing Sheets

ENVELOPE AND PROCUREMENT STAND FOR PLACENTAL TRANSPORT AND STEM CELL COLLECTION

CROSS-REFERENCE TO RELATED APPLICATIONS

This application claims priority to U.S. Provisional Patent Application Ser. No. 61/522,275, filed on Aug. 11, 2011 and entitled "Placental Stem Cell Procurement Stand," and U.S. Provisional Patent Application Ser. No. 61/522,280, filed on Aug. 11, 2011, and entitled "Placental Envelope and Transport Container," the entire disclosures of which are incorporated herein by reference.

BACKGROUND OF THE INVENTION

1. Field of the Invention

The present invention relates to placental stem cells and, more specifically, to devices, systems, and methods for procuring placental stem cells.

2. Description of the Related Art

Stem cells are master cells found in all multicellular organisms. These special cells are important to the human body, for example, because they are capable of differentiating into a multitude of different specialized cell types, and dividing to maintain a supply of stem cells. In humans there are two main types of stems cells: embryonic stem cells and adult stem cells. In a developing embryo stem cells differentiate into all types of cells, thereby creating specialized tissues, organs, and systems. In an adult human, stem cells are involved in the normal turnover of organs such as blood and skin.

Hematopoietic stem cells, for example, are used to treat blood and immune system diseases because they can differentiate into red blood cells, white blood cells, and platelets. However, some stem cell transplants have been performed for patients with genetic or metabolic diseases. Indeed, to date more than 80 different diseases have been treated using stem cell transplants. According to the National Cord Blood Program, there were over 15,000 through the end of 2009. The National Marrow Donor Program estimates that there will be 10,000 cord blood transplants per year by 2015, up from 2,000 per year in 2006.

In addition to known treatments involving stem cells, research continues into the promise of many potential future applications. Indeed, the ability of stem cells to differentiate into other types of cells holds significant promise for treating some of the world's most common diseases including heart disease, diabetes, stroke, hearing loss, blood disorders, Parkinson's disease, and Alzheimer's disease, just to name a few.

Umbilical cord blood—blood which remains in the placenta and umbilical cord after childbirth—is one of the most common sources of stem cells. Since cord blood is collected from the placenta, which is normally discarded, the collection process is safe for both the mother and the newborn. Cord blood is obtained by syringing out the placenta through the umbilical cord shortly after childbirth, after the cord has been detached from the newborn. The retrieved blood can then be frozen and stored indefinitely.

Although the amount of stem cells obtained from cord blood is generally enough to treat a child, there are generally not enough stem cells to treat an adult patient. The placenta is a better source of stem cells, since it can contain up to ten times more stem cells than cord blood. Still, even when blood is retrieved from both the umbilical cord and placenta using current collection methods, the amount of stem cells is often not suitable to treat an adult patient.

As a result, there is a need for cord blood collection methods and devices that significantly increase the number of stem cells collected, facilitate the collection of stem cells, and allow for the collection of enough stem cells to treat at least one adult patient.

BRIEF SUMMARY OF THE INVENTION

It is therefore a principal object and advantage of the present invention to provide a method, device, and/or system for the collection of cord blood.

It is another object and advantage of the present invention to provide a method, device, and/or system to increase the number of stem cells collected from cord blood.

It is yet another object and advantage of the present invention to provide a device for safely and securely transporting a placenta from one location to another, and to provide a device to facilitate the procurement of stem cells from a placenta.

It is a further object and advantage of the present invention to provide a device to facilitate the ingress and egress of stem cell procurement fluids into and out of a placenta.

Other objects and advantages of the present invention will in part be obvious, and in part appear hereinafter.

Systems and devices for transporting or storing a placenta and for collecting stem cells from the placenta. According to one aspect, a stand for preparing and collecting a plurality of stem cells from a placenta comprises: a base positionable in a horizontal orientation and having an upper surface and a lower surface, the upper surface of the base defining a first recess adapted to hold at least a portion of a placenta; an upper platform positionable in a horizontal orientation and having an upper surface and a lower surface, the upper surface of the upper platform defining a second recess adapted to hold at least a portion of a placenta; and a back support coupled to the base and said upper platform such that the upper platform is suspended above the base; wherein the placenta is positioned at least partially in the first recess to receive a stem cell collection solution, and wherein the placenta is positioned at least partially in the second recess to expel at least a portion of the stem cell collection solution and the plurality of stem cells.

In one implementation, the stand comprises a plastic.

In one implementation, the back support comprises an adjustable clip, and the back support can define a series of slots into which the adjustable clip can be placed.

In one implementation, the upper platform defines a slot through the entire thickness of the upper platform and extends from inside the second recess to the outside edge of the upper platform, and is adapted such that an umbilical cord of said placenta can fit into the slot.

In one implementation, the back support is coupled to the upper platform via a hinge such that the upper platform can pivot between a first position wherein the upper platform is parallel to the base, and a second position wherein the upper platform is perpendicular to the base.

In one implementation, the device further comprises a stem cell collection solution container coupled to the stand.

In another aspect, a stand for preparing and collecting a plurality of stem cells from a human placenta comprises: a base positionable in a horizontal orientation and having an upper surface and a lower surface, the upper surface of the base defining a first recess adapted to hold at least a portion of a placenta; an upper platform positionable in a horizontal orientation and having an upper surface and a lower surface, the upper surface of the upper platform defining a second recess adapted to hold at least a portion of a placenta, and further defining a slot through the entire thickness of the upper platform and extending from inside the second recess to the outside edge of the upper platform, the slot adapted such that an umbilical cord of a placenta can fit into the slot; and a back support coupled to the base and the upper platform such that the upper platform is suspended above the base, the back support comprising an adjustable clip and defining a series of slots into which a portion of the adjustable clip can be inserted, wherein the back support is coupled to the upper platform via a hinge such that the upper platform can pivot between a first position wherein the upper platform is parallel to the base and a second position wherein the upper platform is perpendicular to the base; wherein the placenta is positioned at least partially in the first recess to receive a stem cell collection solution, and wherein the placenta is positioned at least partially in the second recess to expel at least a portion of the stem cell collection solution and the plurality of stem cells.

In another aspect, a device for the transport of a placenta, the device comprises: a cylindrical bottom portion defining a first half of a placental storage region; a cylindrical top portion defining a second half of the placental storage region, wherein the cylindrical top portion defines an opening adapted for an umbilical cord, the opening extending through the top portion; and a hinge coupling the cylindrical bottom portion and the cylindrical top portion; wherein the placenta is enclosed inside the placental storage region when the cylindrical top and bottom portions are in a closed configuration.

In one implementation, the cylindrical bottom portion and the cylindrical top portion are domed.

In one implementation, the device comprises a plastic.

In one implementation, the placenta is a human placenta.

In one implementation, the device further comprises securing means adapted to secure the cylindrical top portion and the cylindrical bottom portion in the closed configuration.

In another aspect, a device for the transport of a human placenta comprises a domed cylindrical bottom portion defining a first half of a placental storage region; a domed cylindrical top portion defining a second half of the placental storage region, wherein the cylindrical top portion defines an opening adapted for an umbilical cord, the opening extending through the top portion; a hinge coupling the cylindrical bottom portion and the cylindrical top portion; and securing means adapted to secure the cylindrical top portion and the cylindrical bottom portion in the closed configuration; wherein the placenta is enclosed inside the placental storage region when the cylindrical top and bottom portions are in a closed configuration.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
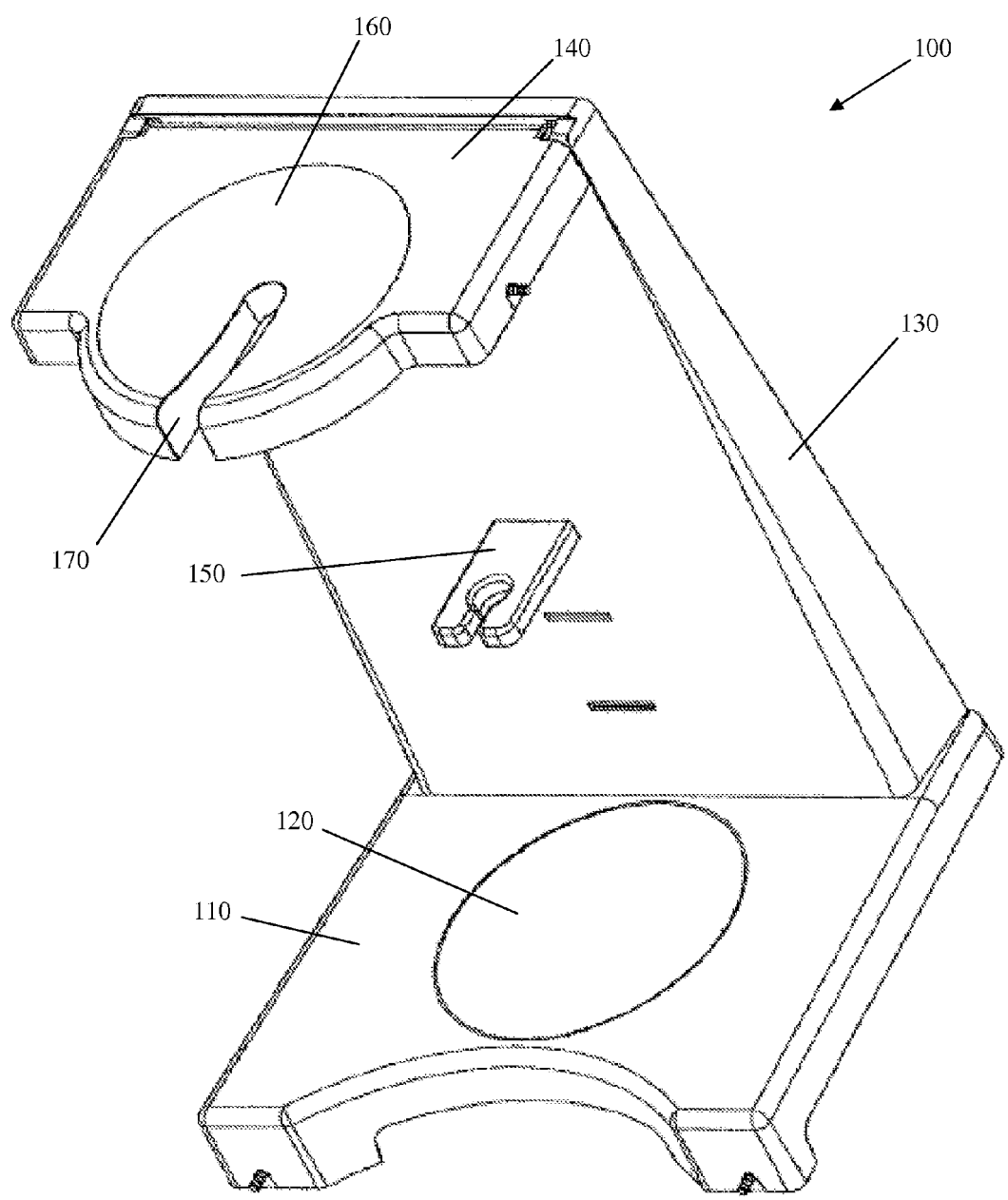
FIG. 1 is a top view of a stem cell procurement stand according to one embodiment of the present invention.
Figure 2:
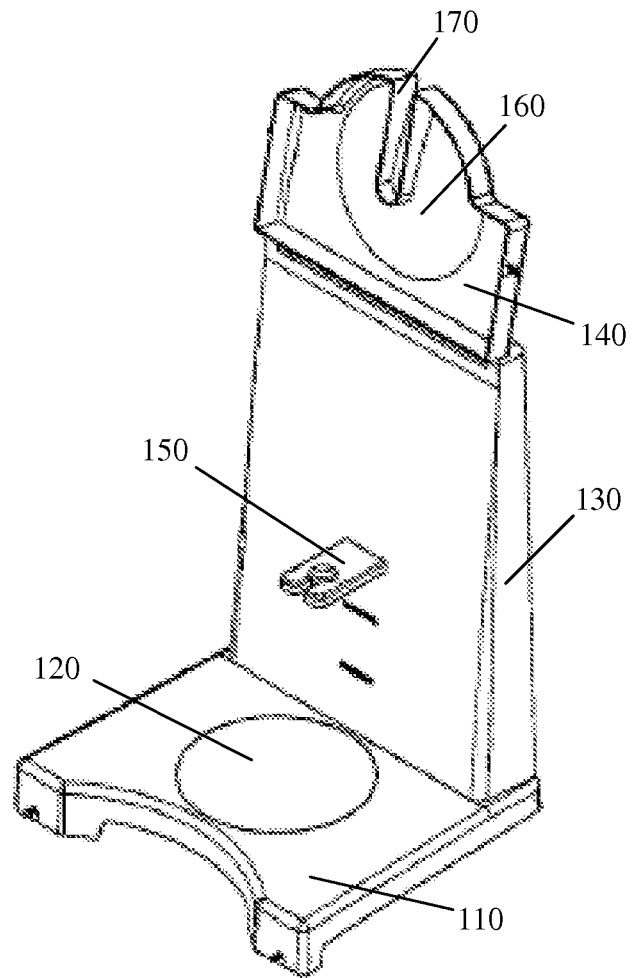
FIG. 2 is several views of a stem cell procurement stand according to one embodiment of the present invention.
Figure 3:
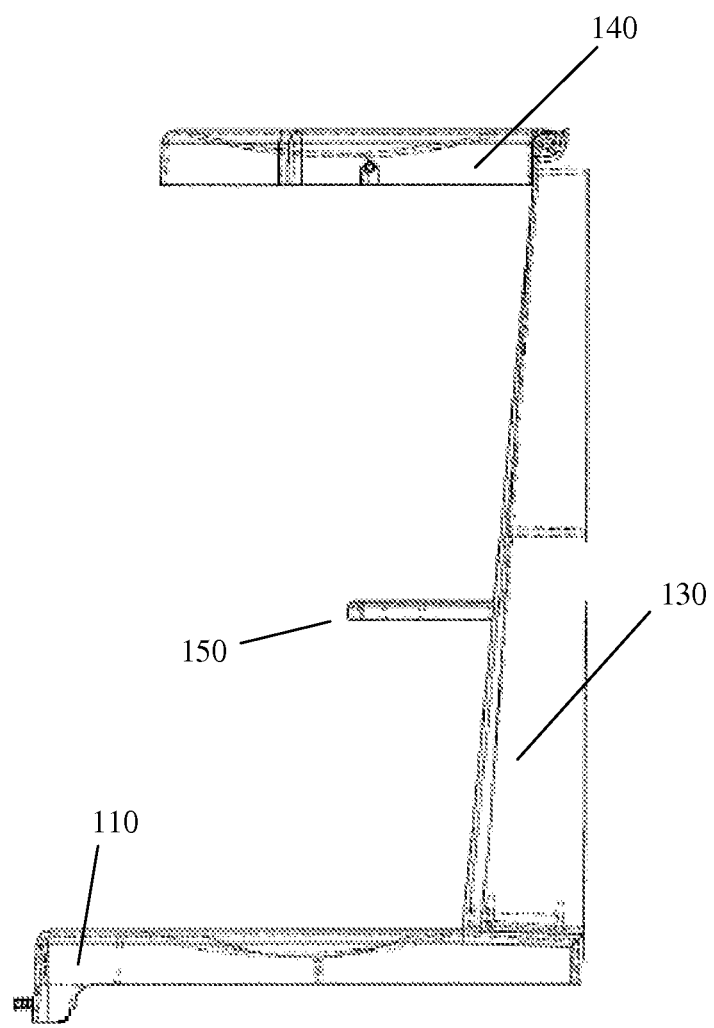
FIG. 3 is a side view of a stem cell procurement stand according to one embodiment of the present invention.
Figure 4:
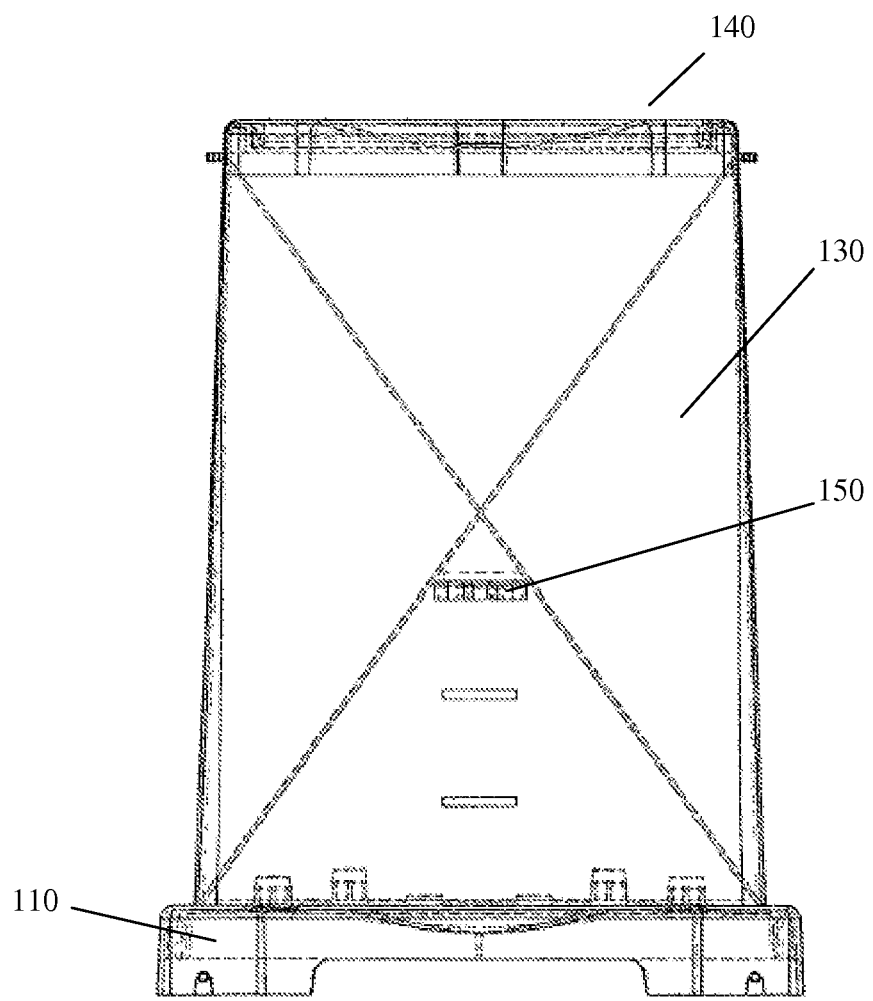
FIG. 4 is a front view of a stem cell procurement stand according to one embodiment of the present invention.

Referring now to the drawings, wherein like reference numerals refer to like parts throughout, there is seen in FIG. 1 a top view of a stem cell procurement stand 100 according to one embodiment, which facilitates the ingress and egress of stem cell procurement fluids into and out of the placenta after delivery. The device preferably comprises a rigid material such as plastic or metal, although a wide range of suitably rigid materials are possible.

Stand 100 comprises a base 110. The base comprises at least a first recess 120 which is preferably dimensioned such that it can comfortably receive a placenta. In a preferred embodiment, the placenta is placed 'umbilical cord side up' to allow fluids to fill the cord and placenta via gravity.

Extending vertically upward from base 110 is the back 130 of the device, which connects the base to an upper portion 140 of the device located near the top of the back. The back 130 optionally comprises a clip 150 for holding a bag or other stem cell procurement equipment. In one embodiment, clip 150 holds a bag containing stem cell procurement fluid which is loaded into the placenta during loading, and holds a bag into which the stem cell procurement fluid is unloaded from the placenta during unloading. Back 130 can further comprise a series of slots positioned up and down the front surface of the back such that the position of the clip can be adjusted, as shown for example in FIG. 1.

Upper portion 140 of the device is positioned at the top of back 130. The upper portion itself comprises at least a first recess 160 which is dimensioned such that it can comfortably receive a placenta, similar to recess 120. In a preferred embodiment, the placenta is placed 'umbilical cord side down' in recess 160 to allow fluids to exit the cord and placenta via gravity. To maximize the effect of gravity, the umbilical cord is preferably positioned into a first slot 170 in recess 160 such that fluids in the placenta can flow toward and into the umbilical cord and then into a collection device such as a bag or other container. In one embodiment, the upper portion 140 is hinged to the back of the device such that it can occupy a first position where the upper portion is roughly parallel with the base (shown in FIG. 1), and a second position where the upper portion is at an angle (0° to 180° or more) compared to the base (shown in FIG. 1).

A wide range of dimensions for the device are possible, although according to one embodiment the dimensions are at least partially derived from the average size of the placenta from the particular mammal it will be used for. For example, if the stand is used for humans, the recesses will be sized to hold at least the average human placenta, and the remainder of the stand will be sized based on the size of the recesses.

Stem cell procurement stand 100 is preferably used to facilitate the loading and unloading of stem cell procurement fluid. At a first step of procurement using the device according to one embodiment, the placenta is placed in lower recess 120 and a bag containing the procurement fluid is clipped onto the device. A needle or tube from the bag is inserted into the umbilical cord and/or placenta, and the fluid from the bag is allowed to load into the placenta via the umbilical cord. The placenta may be manipulated to encourage loading.

At a second step of procurement using stem cell procurement stand 100 according to one embodiment, the placenta is placed in the upper recess 160 of the device with the umbilical cord in the provided slot, and a collection bag is clipped onto the device. A needle or tube from the bag is inserted into the umbilical cord and/or placenta, and the fluid from the placenta is allowed to load into the bag via the umbilical cord. The placenta may be manipulated to encourage unloading.

Figure 5:
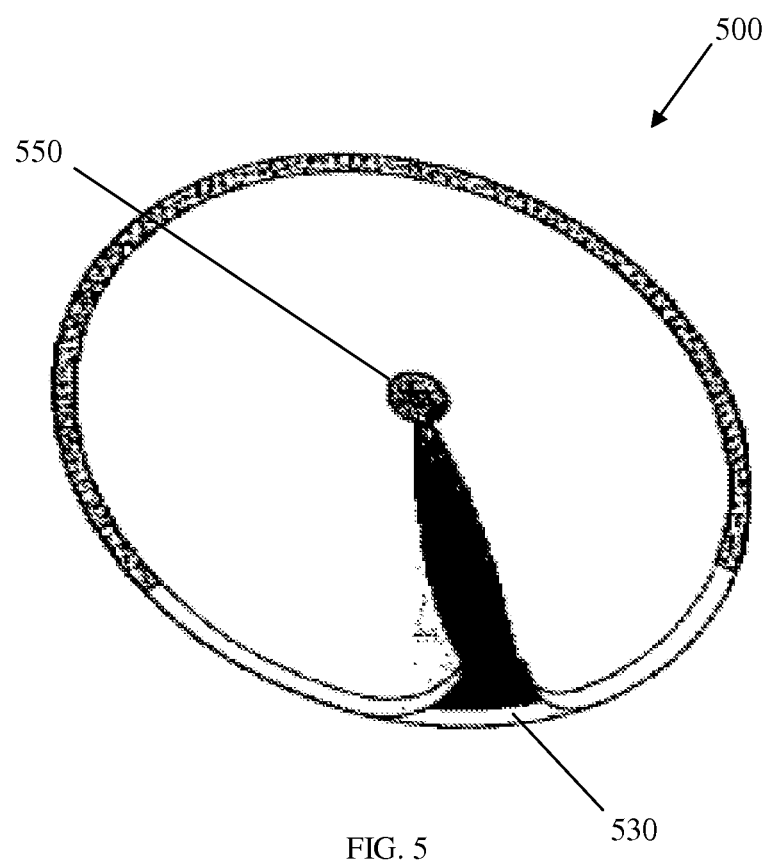
FIG. 5 is a top view of a placental envelope according to one embodiment of the present invention.
Figure 6:
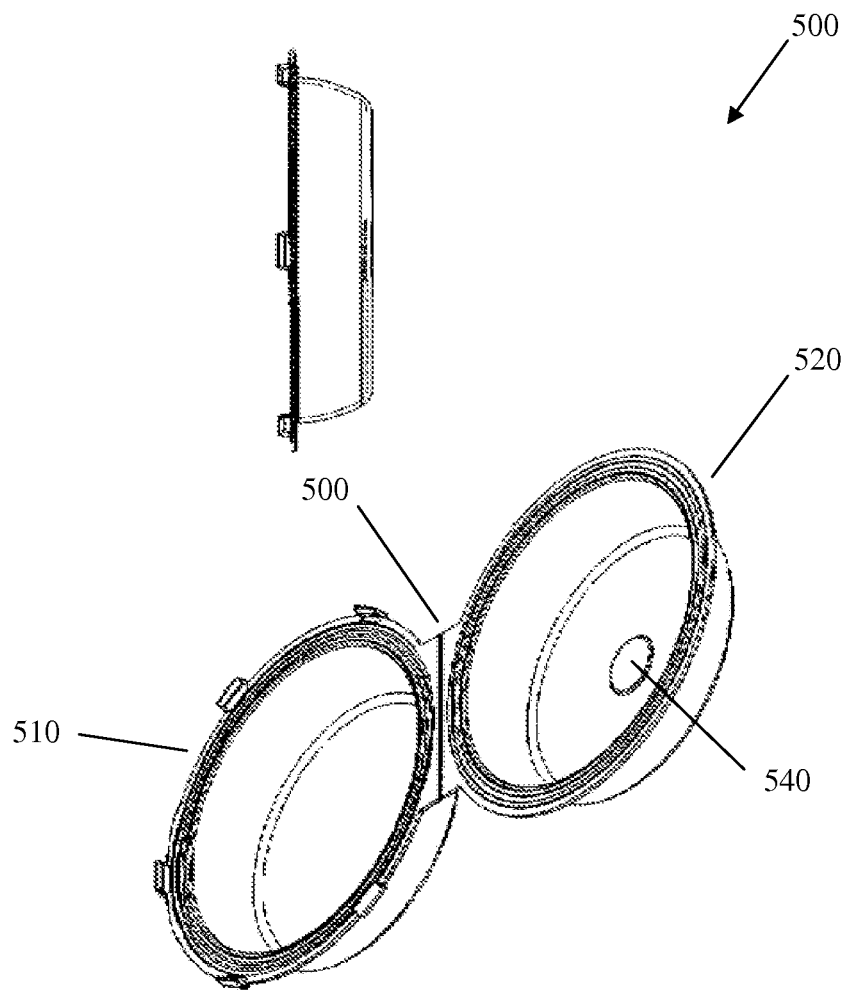
FIG. 6 is several views of a placental carrier according to one embodiment of the present invention.

In addition to facilitating the ingress and egress of stem cell procurement fluids into and out of a placenta, maximizing efficient stem cell collection also often requires the secure transport of the placenta from one location to another. Shown in FIG. 5 is an envelope or carrier 500 which facilitates the safe and secure transport of a placenta and attached umbilical cord. Envelope 500 preferably comprises a rigid material such as plastic or metal, although a wide range of suitably rigid materials are possible.

The placental envelope 500 preferably comprises a domed structure, with a lower dome 510 and an upper dome 520. The upper and lower domes define an inner space into which an average placenta ("average" defined by the mammal from which the placenta will be taken) can comfortably reside. For example, the inner space can be sized to comfortably receive the average human placenta.

The upper and lower dome are usually of equal or similar size such that the edges of the two domes come together and align without creating any overhang, gaps, or other abnormalities. Accordingly, the placental envelope can be secured at its edges—by a latch, a lock, Velcro, tape, a clamp, a pin, a snap, or many other means—to hold the envelope securely closed during transport. Further, the edge of the upper and/or lower dome can comprise a gasket or seal that seals together the two domes the envelope when the envelope is closed. In one embodiment, the envelope comprises a rubber gasket that must be at least partially compressed to complete closure of the envelope, thereby creating a seal.

The upper dome optionally comprises a hole 550 in the top center of the dome, and can include a slot 530 running from the base of the dome to hole 550. According to one embodiment, during loading the umbilical cord slides up through slot 530 and is ultimately positioned such that it exits hole 550. This allows, for example, a clamped umbilical cord to easily fit into the device, as the clamp will typically be larger than the hole. In another embodiment, the upper dome comprises hole 540 in the top center of the dome without the slot, and the umbilical cord is fed through the hole during loading.

Note that the terms "upper" and "lower" in at least one embodiment of the device are used only to provide a frame of reference to the user. In any embodiment where the 'upper' and 'lower' domes are of equal or near-equal proportions, either dome of the placental envelope may be the upper or lower dome.

In one application, placental carrier 500 comprises a top portion 520 and a bottom portion 510 which are not domed, but are shaped to hold a placenta. Top 520 and 510 can be joined by a hinge 560, as shown in the figures. The top portion and the bottom portion, when in a closed configuration, define an inner space into which an average placenta ("average" defined by the mammal from which the placenta will be taken) can comfortably reside. For example, the inner space can be sized to comfortably receive the average human placenta. In one embodiment, the inner space is sized to fit a placenta that has been placed into a first transport container, such as the placental envelope.

The top and bottom portions are usually of equal or similar size such that the edges of the two portions come together and align without creating any overhang, gaps, or other abnormalities. Accordingly, the placental carrier can be secured at its edges—by a latch, a lock, Velcro, tape, a clamp, a pin, a snap, or many other means—to hold the carrier securely closed during transport. In yet another embodiment, the top portion and a bottom portion are separate pieces that can be snapped or joined together by other means, including but not limited to a latch, a lock, Velcro, tape, a clamp, a pin, and a snap, among other means. Further, the edge of the top and/or bottom portions can comprise a gasket or seal that seals together the two portions of the carrier when the carrier is closed. In one embodiment, the carrier comprises a rubber gasket that must be at least partially compressed to complete closure, thereby creating a seal.

In one embodiment, the top and/or bottom portions are rounded and can comprise a lip at their edge. The upper and bottom lips come together when the device is in the closed configuration and can be used to keep the top and bottom portions closed together. For example, the bottom and/or top lips can further comprise a series of clamps or latches that snap onto or over the opposing lip to hold the device in the closed configuration.

Although the present invention has been described in connection with a preferred embodiment, it should be understood that modifications, alterations, and additions can be made to the invention without departing from the scope of the invention as defined by the claims.

What is claimed is:

1. A stand for preparing and collecting a plurality of stem cells from a placenta, the stand comprising:
 a base having an upper surface and a lower surface, said upper surface of said base defining a first recess configured to hold at least a portion of a placenta;
 an upper platform positionable in a parallel, horizontal orientation with regard to the base, the upper platform having an upper surface and a lower surface, said upper surface defining a second recess configured to hold at least a portion of a placenta, and further wherein the upper platform defines a slot through the entire thickness of the upper platform extending from inside the second recess to an outside edge of the upper platform, the slot sized such that an umbilical cord can fit into said slot; and
 a back support coupled to said base and said upper platform such that said upper platform is suspended above said base, wherein said back support comprises a plurality of slots defined along a length thereof, and further including a clip inserted into one of said slots, said clip being moveable from one of the plurality of slots to another of said plurality of slots, wherein said clip is configured to hold a stem cell procurement component.

2. The stand of claim 1, wherein said stand comprises a plastic.

3. The stand of claim 1, wherein said back support is coupled to said upper platform via a hinge such that said upper platform can pivot between a first position wherein said upper platform is parallel to said base, and a second position wherein said upper platform is perpendicular to said base.

4. A stand for preparing and collecting a plurality of stem cells from a human placenta, the stand comprising:
 a base having an upper surface and a lower surface, said upper surface of said base defining a first recess configured to hold at least a portion of a placenta;
 an upper platform positionable in a parallel, horizontal orientation with regard to the base, the upper platform having an upper surface and a lower surface, said upper surface of said upper platform defining a second recess configured to hold at least a portion of a placenta, and further defining a slot through the entire thickness of the upper platform and extending from inside the second recess to the outside edge of the upper platform, the slot adapted such that an umbilical cord of a placenta can fit into said slot; and a back support coupled to said base and said upper platform such that said upper platform is suspended above said base, said back support comprising a plurality of slots defined along a length thereof, and further including a clip inserted into one of said slots, said clip being moveable from one of the plurality of slots to another of said plurality of slots, said clip configured to hold a stem cell procurement component, and further wherein said back support is coupled to said upper platform via a hinge such that said upper platform can pivot between a first position wherein said upper platform is parallel to said base and a second position wherein said upper platform is perpendicular to said base.

* * * * *